(12) United States Patent
Kerr

(10) Patent No.: US 8,512,631 B2
(45) Date of Patent: *Aug. 20, 2013

(54) SANITIZATION DEVICES AND METHODS OF THEIR USE

(76) Inventor: James Kerr, Old Orchard Beach, ME (US)

( * ) Notice: Subject to any disclaimer, the term of this patent is extended or adjusted under 35 U.S.C. 154(b) by 121 days.

This patent is subject to a terminal disclaimer.

(21) Appl. No.: 13/043,702

(22) Filed: Mar. 9, 2011

(65) Prior Publication Data

US 2012/0230867 A1    Sep. 13, 2012

(51) Int. Cl.
  *A61L 2/10*  (2006.01)
(52) U.S. Cl.
  USPC ............................................. 422/24; 422/22
(58) Field of Classification Search
  USPC ..................................................... 422/22, 24
  See application file for complete search history.

(56) References Cited

U.S. PATENT DOCUMENTS

| 4,425,677 | A  |   | 1/1984  | Cox |  |
|---|---|---|---|---|---|
| 4,866,805 | A  |   | 9/1989  | Oden et al. | |
| 4,922,578 | A  |   | 5/1990  | Miettinen | |
| 5,071,628 | A  |   | 12/1991 | Alazet | |
| 5,297,309 | A  |   | 3/1994  | Rotoli | |
| 5,950,269 | A  |   | 9/1999  | Openshaw et al. | |
| 6,053,354 | A  | * | 4/2000  | Niemeyer | 220/819 |
| 6,146,588 | A  |   | 11/2000 | Deighton | |
| 6,651,288 | B1 |   | 11/2003 | Hackett | |
| 6,749,918 | B2 |   | 6/2004  | Staal | |
| 6,752,957 | B1 | * | 6/2004  | De Lasa et al. | 422/22 |
| 6,849,233 | B2 | * | 2/2005  | Bushnell et al. | 422/24 |
| 6,886,210 | B2 |   | 5/2005  | Dean | |
| 8,143,596 | B2 |   | 3/2012  | Yerby | |
| 2003/0031586 | A1 | * | 2/2003 | Eckhardt et al. | 422/24 |
| 2004/0078909 | A1 |  | 4/2004 | Coppa | |
| 2004/0168274 | A1 |  | 9/2004 | Greely | |
| 2005/0160549 | A1 |  | 7/2005 | Dean | |
| 2007/0098653 | A1 | * | 5/2007 | Tamasawa et al. | 424/59 |
| 2007/0164232 | A1 |  | 7/2007 | Rolleri et al. | |
| 2008/0104782 | A1 |  | 5/2008 | Hughes | |
| 2009/0065716 | A1 |  | 3/2009 | Ullman | |
| 2010/0104470 | A1 |  | 4/2010 | McCabe | |
| 2010/0193709 | A1 |  | 8/2010 | Dalton | |

FOREIGN PATENT DOCUMENTS

| JP | 10-052480 | * | 2/1998 |
|---|---|---|---|
| WO | 88/03775 A1 | | 6/1988 |
| WO | 97/28733 A1 | | 8/1997 |
| WO | 00/76388 A1 | | 12/2000 |
| WO | 00/78021 A1 | | 12/2000 |

(Continued)

OTHER PUBLICATIONS

English Machine Translation of JP-10-052480 Kato et al. Feb. 24, 1998 provided by Industrial Property Digital Library.*

(Continued)

*Primary Examiner* — Sean E Conley
*Assistant Examiner* — Donald Spamer

(57) ABSTRACT

The present invention relates to sanitization devices and methods. More particularly, the invention relates to devices and methods that significantly reduce or eliminate germs, bacteria and/or other microorganisms from objects such as bags, purses, footwear or other objects, as well as bare feet, hands, paws, hooves or other anatomical surfaces, which come into contact with them. The device and method uses germicidal radiation which exposes only the areas of the object that come into applied contact with the device. A top platform of the devices may be in a tilted position when not in uses.

4 Claims, 4 Drawing Sheets

(56) References Cited

FOREIGN PATENT DOCUMENTS

| | | |
|---|---|---|
| WO | 2009/088379 A1 | 7/2009 |
| WO | 2009/147263 A1 | 12/2009 |

OTHER PUBLICATIONS

U.S. Appl. No. 13/589,105, filed Aug. 2012, Kerr.*
U.S. Appl. No. 13/344,076, filed Jan. 2012, Kerr.*

* cited by examiner

SANITIZATION DEVICES AND METHODS OF THEIR USE

FIELD OF INVENTION

The present invention relates to sanitization devices and methods. More particularly, the invention relates to devices and methods that significantly reduce or eliminate germs, bacteria and/or other microorganisms from objects such as bags, purses, footwear or other objects, as well as bare feet, hands, paws, hooves or other anatomical surfaces, which come into contact with them. The device and method uses germicidal radiation which exposes only the areas of the object that come into contact with the device.

BACKGROUND OF THE INVENTION

Bacteria, viruses, germs, molds, fungi and other undesirable microorganisms are transferred from one area to another through contact with people, animals and objects that come into contact with them.

The present invention is concerned with the problem of spreading microorganisms that are carried on the outer surfaces of footwear and other objects as well as hands, feet, paws, hooves and other anatomical surfaces that have been exposed to areas contaminated with undesirable microorganisms. The outer bottom surfaces of footwear such as soles and heels can come into contact with floor areas or outdoor ground areas that may be unsanitary and contaminated with microorganisms such as bacteria, viruses, germs molds, and fungi. Areas where such microbial contamination commonly exists include hospital areas, such as emergency rooms, food handling areas such as food markets, restaurants, recycling areas, and refuse dumps as well as public toilets, public sidewalks and streets, handrails on staircases and escalators, parks, park benches, farms, or anywhere that the public frequents. Someone or something that has been contaminated with an undesirable microorganism can easily and unknowingly spread the microorganisms around. In some cases the contamination can result from urine in areas near public toilets and urinals, animal urine and feces as well as human sputum on sidewalks, streets, lawns, etc.

The outer surfaces of other objects such as suitcases, handbags, purses, briefcases, packages, and the like which come into contact with such contaminated areas as airport bathrooms, bars, and restaurants which may expose them to domestic and international microorganisms also become contaminated and thereby become a source of further microbial contamination. Thus, footwear and other objects can carry microorganisms into the home, office, car or other personal areas.

Further, house pets that have come into contact with contaminated areas such as parks, yards, and the like can also carry undesirable microorganisms into the home. In livestock areas cattle, horses, sheep and the like constantly come into contact with undesirable microorganisms and spread them around on the paws, hooves or feet.

In all these scenarios, a person's hands may also become contaminated by touching a contaminated area. This will result in the transfer of the pathogenic microorganisms into the body through subsequent touching of the mouth, eyes, ears, and such. Similarly, bare feet can be exposed to microorganism contamination when walking bare foot outside or in locker rooms, pools, showers and the like and further spread them.

It is therefore highly desirable to eliminate or significantly reduce the amounts of these microbes from surfaces that carry them.

Solutions to this problem have been disclosed whereby devices containing fluid disinfectants either wet the bottom of footwear through sponge applications or a disinfectant is sprayed onto the bottom of footwear. The solutions create other problems such as slippery soles, tracking of the fluids and potential exposure to toxic materials relating to the disinfectant. A dry method would thus be more desirable.

A device described in US Pat. Appl. 2010/0193709 utilizes a platform that is transparent to UVC sanitizing radiation uses to disinfect a shoe or foot. The transparent platform is made of glass which blocks a certain portion of the UV light with only a remainder of the light illuminating the shoe or foot. The platform may also be a metal grid allowing for the UVC light to shine through. The application also describes a cover that the feet or shoes go into so that any stray UVC light does not escape. The glass used in this application blocks the disinfecting UVC wavelength of 254 nm and allows through the non-disinfecting UVB and UVA wavelengths and is therefore not suitable for disinfecting applications. The cover in this application presents a tripping hazard as well as an imperfect cover for blocking stray UVC light.

A device described in US Pat Appl. 2010/0104470 describes a device that uses a UV light along with a platform preferably made of Plexiglas and a "soft plastic material" on top of the platform with a gel between the plastic and the Plexiglas that is absorptive of the UV light. When a shoe steps on the platform the gel will be pushed aside and the UV will shine through the Plexiglas, the "soft plastic material" and onto the sole of the shoe. Radiation with germicidal activity is 254 nm which will not pass through Plexiglas which is polymethylmethacrylate. Although the application states other transparent materials can be used for the platform, no enabling materials are described therefore leaving those skilled in the art to perform a substantial amount of research to find suitable materials. Additionally, the application states "soft plastic materials" that are substantially transparent to the disinfecting radiation can be used, without any suggestion as to what those materials might be, again leaving it to the practitioner to perform a substantial amount of research to determine a material which is soft, pliable and transparent to the disinfecting radiation, which again is 254 nm. While many gels absorb radiation there, not any gel will be suitable for this application. The gel needs to have to correct viscosity so that it will push away when pressure is applied but not be so viscous that when pressure is removed, the gel will flow back into the area creating a substantially uniform thickness ready for the next shoe to disinfect.

Thus more efficient devices and methods and more suitable materials are needed to properly eliminate or significantly reduce undesirable microorganisms. Additionally these are no provisions for hands sanitation, house pet sanitation or other animal sanitation.

SUMMARY OF THE EXEMPLARY EMBODIMENTS

It is an object of the current invention to overcome the deficiencies commonly associated with the prior art as discussed above and provide devices and methods that eliminate or significantly reduce undesirable microorganisms from objects such as bags, purses, footwear or other objects, as well as bare feet, hands, paws, hooves or other anatomical surfaces.

In one embodiment, a device is provided for the elimination or significant reduction of undesirable microorganisms from objects which contains a housing having a bottom platform, sides and a top platform. The top platform contains a top layer made of a deformable UVC transparent fluorinated film, a bottom layer made from UVC transparent quartz, and sides, with a UVC absorbent liquid contained in the top platform between the top layer and the bottom layer. The device has one or more UVC emitting devices situated in the housing, between the bottom platform and the top platform.

In a second embodiment, a device is provided for the elimination or significant reduction of undesirable microorganisms from objects which contains a housing having a bottom platform, sides and a top platform. The top platform contains a top layer made of a deformable UVC transparent fluorinated film, a bottom layer having a support layer upon which is positioned a UVC transparent quartz, sides, with a UVC absorbent liquid contained in the top platform between the top layer and the bottom layer. The support layer is perforated to allow UVC light to pass through. The device has one or more UVC emitting devices situated in the housing, between the bottom platform and the top platform.

In a third embodiment, a device is provided for the elimination or significant reduction of undesirable microorganisms from objects which contains a housing having a bottom platform, sides and a top platform. The top platform contains a bottom layer made from UVC transparent quartz, sides, and a bag fitting in the volume made from the bottom layer and the sides which is made of a deformable UVC transparent fluorinated film, the bag containing a UVC absorbent liquid. The device has one or more UVC emitting devices situated in the housing, between the bottom platform and the top platform.

In a fourth embodiment, a device is provided for the elimination or significant reduction of undesirable microorganisms from objects which contains a housing having a bottom platform, sides and a top platform. The top platform contains a bottom layer having a support layer upon which is positioned a UVC transparent quartz, sides, and a bag fitting in the volume made from the bottom layer and the sides which is made of a deformable UVC transparent fluorinated film, the bag containing a UVC absorbent liquid. The support layer is perforated to allow UVC light to pass through. The device has one or more UVC emitting devices situated in the housing, between the bottom platform and the top platform.

In further embodiments the top platform of the devices in the above embodiments are attached to the housing by hinging mechanisms and spring mechanisms which allow the top platform to tilt up and down when pressure is removed or applied, respectively.

In still a further embodiment, a device is provided for the elimination or significant reduction of undesirable microorganisms from objects which contains a housing having a bottom platform, sides and a top platform. The top platform contains a bottom layer having a support layer, sides, and a bag fitting in the volume made from the bottom layer and the sides which is made of a deformable UVC transparent fluorinated film, the bag containing a UVC absorbent liquid. The support layer is perforated to allow UVC light to pass through. The device has one or more UVC emitting devices situated in the housing, between the bottom platform and the top platform.

In each of the above embodiments a device for removing debris may be attached to the house.

In each of the above embodiments the viscosity of the UVC absorbing liquid is between about 1 to about 500 centipoises.

DETAILED DESCRIPTION OF THE INVENTION

As used herein the term UVC refers to electromagnetic radiation with wavelengths ranging between 200-280 nanometers, inclusively.

As used herein the term tilted means non-horizontal wherein one side is higher than the other.

As used herein the terms fluoropolymer, fluorinated film and perfluoro polymer films refer to materials that contain fluorine atoms bonded to carbon in the polymer and/or film.

As used herein the term absorbent refers to the property of a material that prevents at least 85% of the specific radiation wavelength from being transmitted at a chosen thickness of the material.

As used herein the term transmission refers to the property of a material that allows at least 85% of the specific radiation wavelength to be transmitted at a chosen thickness of the material.

Figure 1:
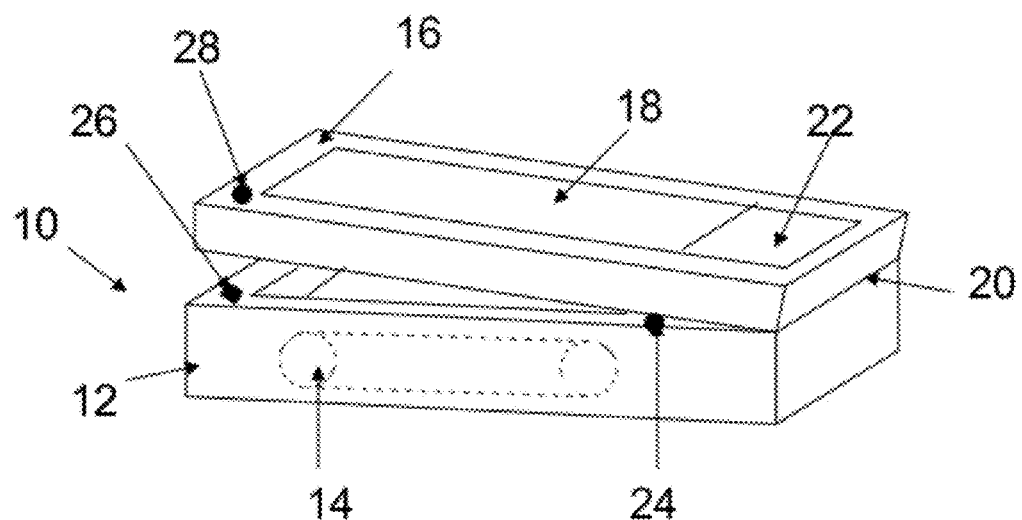
FIG. 1 is an oblique view of one of the exemplary embodiments showing the top platform in a tilted position when not in use.
Figure 2:
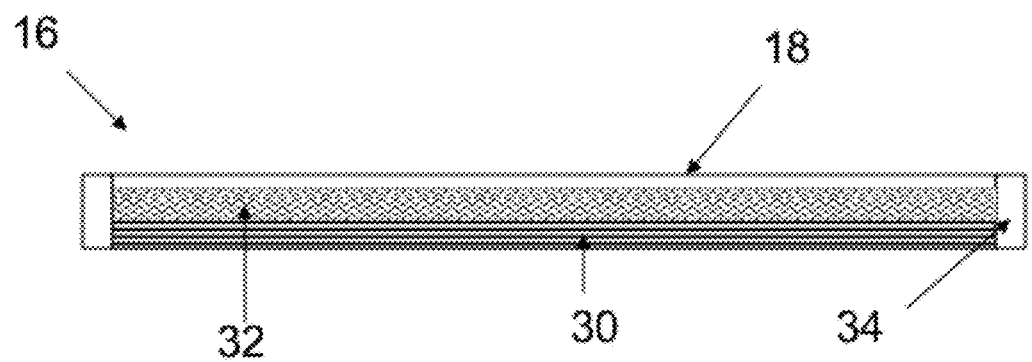
FIG. 2 is a cross sectional view of the top platform showing the top layer 18, the bottom layer 30 and the UVC absorbing liquid 32.

FIG. 1 shows an exemplary embodiment of the current invention 10. A housing 12 containing a bottom and sidewalls contains one or more UVC emitting lamps 14. The housing 12 may be made from any of a number of structural materials well known in the art including, for example, plastic, metal, wood and other structural material. The one or more UVC lamps 14 predominantly emit a wavelength of 254 nm. The sidewalls could be vertical or could be slanted in or out depending on the desired design of the device. The device may be of any desirable geometric shape including, for example, circular, oval, square, rectangular, triangular or other polygonal shape.

The most effective wavelength for killing or inactivating microorganisms is the 100-290-nm range, which is the UVC wavelength band. It is composed of short wavelengths from 200 to 280 nm. Most commercially available UVC lamps are low pressure mercury vapor lamps that give off a wavelength of 254 nm, which is near the optimum for killing or inactivating microorganisms. Low-pressure mercury-vapor lamps usually are made with a quartz bulb in order to allow the transmission of short wavelength light. Natural quartz allows the 254 nm wavelength to pass through but blocks the 184 nm wavelength. Synthetic quartz may also be used which allows the 184 nm wavelength to pass, however 184 nm can produce ozone. The lamps are generally doped with materials that suppress or eliminate the 184 nm wavelengths in low-pressure mercury vapor lamps.

Not to be held to theory, a wavelength of 254 nm UV will break down the molecular bonds within the DNA of microorganisms producing thymine dimers in their DNA thereby destroying them, rendering them harmless or prohibiting growth and reproduction. It is a process similar to the UV effect of longer wavelengths UVB on humans. However UVB and UVA do not act as sanitizing radiations.

As an example, commercially available T5 size UVC germicidal lamps range in input power from about 7-16 watts for a tube which is 11.3 inches long. Output wattage for these lamps, consisting primarily of 254 nm emissions, is approximately 2-4 watts with an efficiency rating of between about 20 and about 40 $\mu W/cm^2$ at a distance of 1 meter from the tube. Power intensity of approximately 1400 to 2800 $\mu W/cm^2$ measured at a distance of 2 inches from the bulb surface is achieved.

Again not to be held to theory, it has been reported that to reach a 99% kill rate of *bacillus anthracis* a dosage of 8,700 $\mu W$ second/$cm^2$ is required. Thus, in the current example and using the equation: Intensity×Exposure Time=$\mu W$ second/$cm^2$, a lamp with a minimum power intensity of 1400 $\mu/cm^2$ at 2 inches from the bulb surface, an exposure time of less than 7 seconds is required. Of course a longer time will improve the kill rate for *bacillus anthracis*. Other notable 99% kill rate exposure requirements for UVC (measured in $\mu W/cm^2$) are: *E-coli*=6500, *Salmonella typhosa*=6000, Dysentery=4200 and Cholera=6500. It should be noted that in the example a 7 second exposure would be sufficient to provide a 99% kill rate of all the aforementioned bacteria. Viruses are also killed by UVC, some of the toughest being poliovirus and rotavirus, which require 21,000 $\mu W/cm^2$ for a 99% kill rate. Thus using the lamps of the above example, a 15 second exposure would provide a 99% kill rate. Also molds and yeasts can be killed by UVC exposure.

FIG. 1 also shows top platform 16 in a tilted position as an exemplary embodiment of the invention, a top layer of the platform 18, a means for hinging 20 the top platform to the sidewall of the housing, a reservoir of UVC absorbing liquid 22, a means for returning the platform to a tilted position 24, a switch 26, and a signal light 28.

The means for hinging 20 may include for example hinges, pivots, springs, hooks, junctions, unions and other hinging mechanisms.

The means for returning the platform to a tilted position 24 includes, for example, spring attachments including spring clips which become depressed when pressure is applied and spring back when pressure is removed, pulley systems, hydraulic mechanisms, air pistons and other means well know in the art. The switch 26 turns the UVC lamp or lamps on when pressure is applied to the top platform. The switch also turns off the UVC lamp when pressure is removed. There may optionally be a time delay between when the switch becomes depressed and when the lamp is turned on, such delays allows the top platform to become closed and the UVC absorbing liquid to flow around the areas which as not intended to be transparent to the UVC emission. The signal light 28 alerts the user that the device has been activated and that the UVC lamps are emitting radiation, the signal light also alerting the user when the lights are turned off and that it is safe to remove the object being sanitized. The signal light 28 may also be an auditory signal.

The top platform 16 is further illustrated in a cut away view in FIG. 2. A top layer 18, a bottom layer 30 and a liquid layer 32 along with sidewalls 34 are shown. The top platform 18 is transparent to 254 nm radiation so that any object placed on top of the top layer 18 will receive the desired dosage of radiation. This layer is deformable so that, in operation when pressure is applied, the top layer will push the liquid aside and reach the bottom layer 30. The top layer 18 may be any of the films that are mechanically tough to withstand repeated wear and that are transparent to UVC radiation. Typical materials are the perfluoro polymer films available from DuPont® such as Teflon® and FEP (fluorinated ethylene propylene) films. As Teflon® becomes thicker its appearance becomes "milky" to visible light. FEP films are clearer films than Teflon® and are less presupposed to scattering. The films are mechanically tough and stretchable and can readily be adapted for manufacturing of the current device.

The bottom layer 30 has the strength to withstand the weight of an object such as a person standing on the device, such as, for example, 300 or more pounds. It has surprisingly been found that Plexiglas, polymethylmethacrylate, which has been described previously, can withstand 300 or more pounds but is not suitable for sanitization application since Plexiglas absorbs the UVC wavelengths which are need to kill the microorganisms of interest. Some specialty polymer films such as high-performance amorphous ethylene copolymer are 20% transparent to UVC at a thickness of 2 mm. However in order to be used in a support layer the thickness needs to be significantly larger. According to such physical laws as the Beers-Lambert law the absorbance of a material increases proportionally to the thickness of the material, and by association the transmittance decreases. Normal glass, such as plate glass or borosilicate glass, can not be used in the devices designed to be sanitizing devices as they block essentially all of the useful UVC radiation. Research has found that quartz is a suitable material for the device. When thick enough quartz can withstand 300 or more pounds and is over 95% transparent to UVC radiation. A support layer may be positioned under the quartz bottom layer of the top platform. The support layer is perforated to allow the UVC light to pass through. The thickness of the support layer is selected to add strength to the top platform and allow for a reduction in the thickness of quartz bottom layer. The support layer may be configured for example, as a honeycomb or open crosshatch and be for example, 1 cm thick. The thickness of the mesh support may vary depending on the amount of weight the device is required to support. The mesh layer is designed to optimize the amount of UVC radiation passed through it and onto the surfaces to be sanitized.

The liquid layer 32 is any liquid which can readily flow when pressure is applied and which essentially absorbs UVC radiation. The liquid is between 1 and 500 centipoise which will allow it to flow when either pressure is applied or when gravity causes it to flow. Materials such as silicon fluids are suitable as the UVC absorbing liquid.

The top platform may include removable bag, as shown in FIG. 3, made from UVC transparent fluoropolymers 18 including, for example, Teflon® and FEP film available from DuPont. The bag contains the UVC absorbing liquid 32 which again has a viscosity that allows for the liquid to move around in response to pressure and will return to its original position when the pressure is removed. A removable bag would allow for replacement of the bag when necessary, for example, in case the surface becomes scuffed and the sanitization process becomes inefficient, for example, if the UVC emission becomes absorbed or diffused away from its intended target. Also if there is a leak somewhere in the top platform a replacement bag may be used to eliminate the problem. The bag may include a means for attachment to the device and have a volume large enough to fit into the area defined by the quartz bottom layer and the sidewalls. As an example, an exemplary bottom layer is 18" by 18" with sidewall of 0.25". The volume is thus 648 cubic inches or 1325 milliliters. A bag with dimensions of 18" long by 18" wide by 0.25" deep will hold 1325 milliliters of the UVC absorbing liquid and fit snuggly in the cavity of the top platform defined by the bottom layer and sidewall. In the case where the top platform is situated in a tilted position, the liquid will flow toward the lower end of the bag and be stored there. The bag will be flexible enough to remain attached to the sidewalls of the top platform but will deform to allow the liquid to flow into and out of the reservoir. The bag may be used either with a quartz bottom layer or a supported quartz bottom layer.

Figure 4:
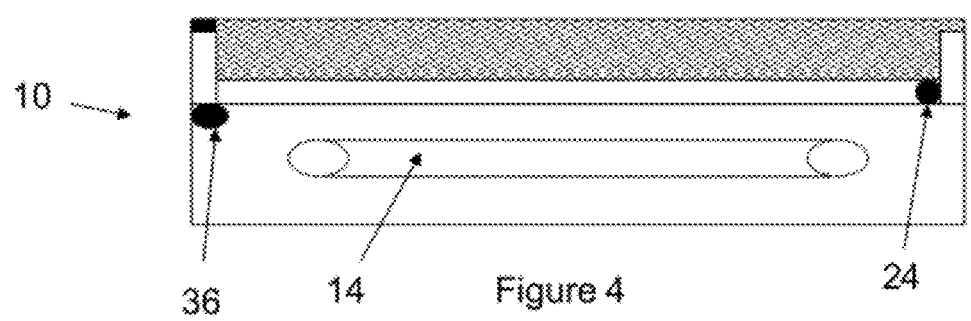
FIG. 4 shows a side view of the device in a closed position.

FIG. 4 shows the device with the top platform in a closed position. A sensor 36 is provided to measure the dosage of the UVC lamp 14 and is connected to a switch that will turn the lamp off when a pre-selected dosage has been reached. This system allows for issues relating to fluctuating output from the lamp due to the lamp's age and from power fluctuations that will effect the lamps output. With this system the lamps will stay on until the desired selected dosage has been reached and the desired amount of microorganisms has been killed.

Figure 5:
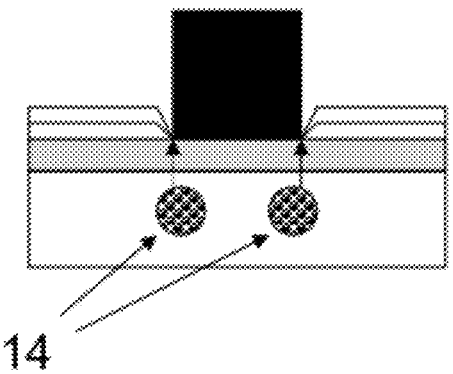
FIG. 5 shows the position of the UVC emitting devices when positioned underneath the area where the object has been places and the UVC liquid has been removed.
Figure 6:
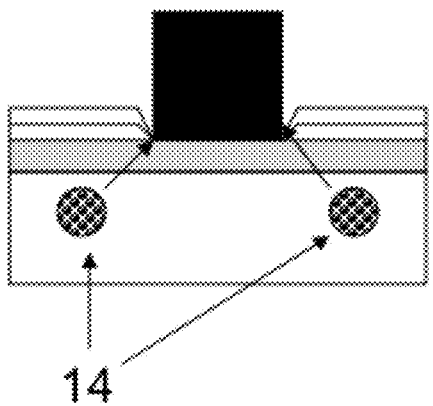
FIG. 6 shows the position of the UVC emitting devices when positioned at an oblique angle to the area where the object has been places and the UVC liquid has been removed.

The UVC lamps 14 may be situated directly under the areas object to be sanitized, FIG. 5, or they may be situated at an angle from such areas as in FIG. 6. The position of the lamps is chosen so as to allow more or less UVC light from escaping the housing.

The device may include a cleaning surface such as for example, a mat, a cloth or anther area which is designed to remove dirt, duct and any debris that might hinder the UVC emission from exposing the surface of the object intended for sanitizing.

The device may further comprise a flap attached to the outside of the sidewalls of the top platform to help prevent any extraneous UVC radiation from escaping.

A further exemplary embodiment is the previously described device wherein the top platform is permanently attached to the sidewalls of the housing and not allowed to be in a tilted position. The benefit of a non-tilting top platform can be realized when the UVC absorbing liquid can readily flow away from the areas that press down onto the top platform.

Figure 7:
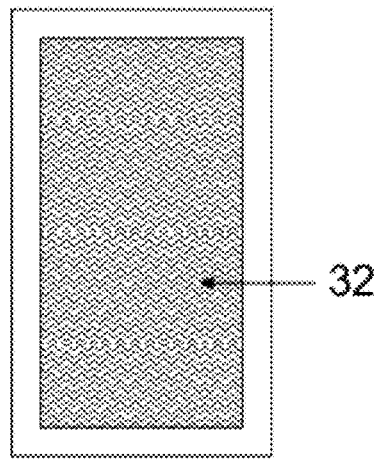
FIG. 7 shows a top view of the top platform when the top platform is positioned against the housing showing the UVC liquid 38 covering the bottom of the top platform.
Figure 9:
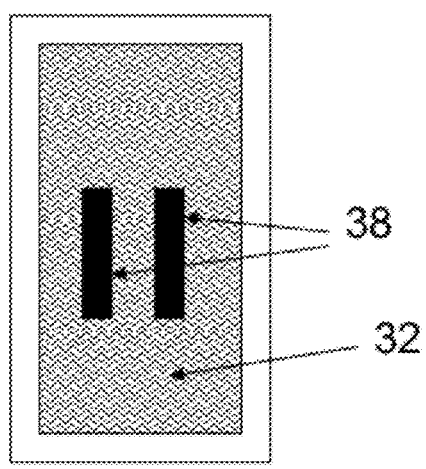
FIG. 9 shows a top view of the top platform when the top platform is positioned against the housing and an object has been placed on the top platform with the UVC liquid 38 surrounding the object.

An object to be sanitized is placed on the top surface of the top platform of the device and the pressure of the object, or an auxiliary pressure such as, for example, when a person holding the object presses down on the object, enough pressure is applied to cause the UVC absorbing liquid to flow away from these pressure areas allowing the top layer to either fully or partially coming into contact with the quartz glass bottom layer. FIG. 7 shows a top view of the top platform of the device when the top platform is permanently attached to the housing with the UVC absorbing liquid 32 covering the bottom quartz layer. FIG. 9 shows a top view of the top platform of the device when an object 38 is placed onto the top platform and the UVC liquid has been displaced by the object. The switch turns the UVC lamps on allowing the sanitizing radiation to pass through the quartz bottom layer and the fluoropolymer top layer to expose the bottom of the object and thereby cause microorganisms to be killed to a desire preselected level. A sensor residing inside the housing, upon which the UVC light directly impinges, measures the dosage of radiation and shuts off the lamps when the desired dosage has been reached. An indicator light is turned on when the UVC lamps are turned on, or makes a noise if an auditory signal device is present, and the light turns off when the UVC lamps are turned off.

Figure 8:
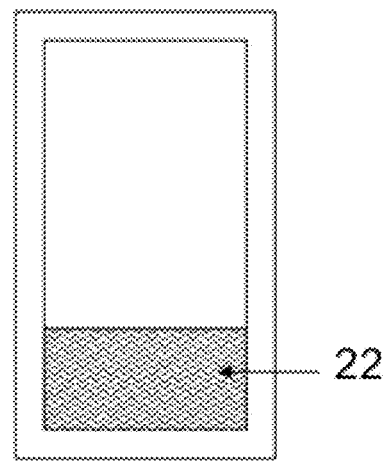
FIG. 8 shows a top view of the top platform when the top platform is positioned in a tilted position showing the UVC liquid 22 having flowed to the lower side of the top platform.
Figure 10:
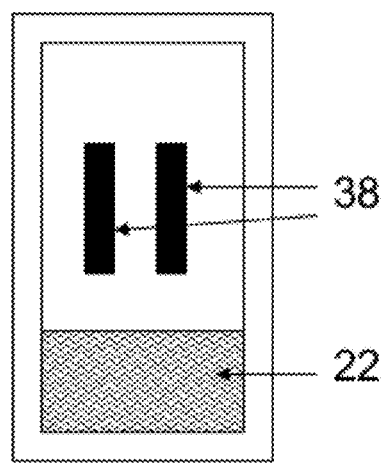
FIG. 10 shows a top of the top platform when the top platform is positioned in a tilted position and an object is placed on the platform just prior to applying pressure to lower the platform into a horizontal position against the housing, also showing the UVC liquid residing in the tilted position.

When the device has a hinged top platform and the top platform is positioned in a tilted position when not in use, an object is placed on the top surface of the top platform and pressure is applied to close the top platform. FIG. 8 shows a top view of the top platform of the device when the top platform is positioned in a tilted position with the UVC absorbing liquid 22 having flowed to the lower, attached, end of the top platform. FIG. 10 show a top view of the top platform of the device with the objects 38 initially position on the top platform with little or no pressure being applied. FIG. 9 show a top view of the top platform with the objects 38 having put enough pressure on the top platform to push the top platform down allowing the UVC absorbing liquid 32 to flow around the object. The bottom of the object will be supported by the bottom quartz layer of the top platform as well as the top fluoropolymer plastic sheet. When not in use there is no opaque liquid in between the bottom and top layer, but when the top platform is pressed downward and comes into contact with the wide walls of the housing the UVC absorbing liquid, which has resided in an optional reservoir then flows out and around the bottom of the object that has been pressed against the top surface, such top surface is also pressed against the bottom quartz layer. The platform springs back to a non-horizontal position allowing the fluid to flow toward the hinged side of the top platform and can be held in an optional reservoir. In this configuration the liquid does not need to "squeezed" away from the object, but instead the liquid flows around the bottom of the object.

Figure 3:
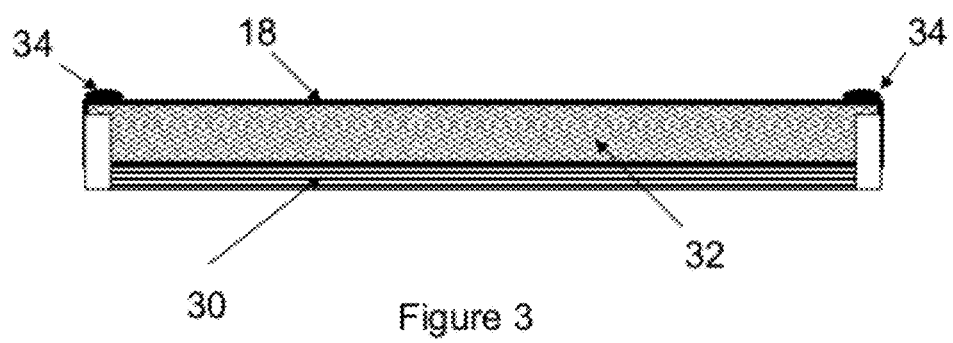
FIG. 3 shows a cross sectional view of the top platform showing a bag 18 containing the UVC absorbing liquid 32 positioned into the cavity of the top platform defined by the bottom layer 30 and the sidewalls.

The top platform of the invention may not contain any quartz layers at all. In this case the perforated support layer is the sole bottom layer of the top platform and has the same characteristics as aforementioned. A removable bag, as shown in FIG. 3, made from UVC transparent fluoropolymers 18 including, for example, Teflon® and FEP film available from DuPont is positioned on top of the support layer. The perforations of the support layer are designed and situated to allow the bag film material to span the opens in the support layer.

The aforementioned pressure can be applied by way of stepping on the top platform, placing one's hands on the platform or placing an object on the platform such that the top platform reaches a horizontal position. When the platform reaches a horizontal position, the housing obtains an enclosed configuration such that radiation emitting from the UVC emitting lamp can not escape. The only places which are exposed to UVC radiation are the areas where the pressure was applied. As a further protection against escaping UVC radiation, a UVC absorbing flap may optionally be attached to the sides of the top platform extending downward so that when pressure is applied to the top platform and it reaches a horizontal position to enclose the UVC lamp, the flats extend below the junction of the top platform and the sides of the housing.

Objects that may be sanitizing by the current devices and methods includes bags, handbags, purses, footwear or other objects, as well as bare feet, hands, paws, hooves or other anatomical surfaces. The devices and methods are also ssuitable for house pets and farm animals such as horses.

What is claimed is:

1. A device for sanitizing objects, comprising:
   a. a housing comprising a bottom platform and sidewalls that enclose the sides of the housing and a top platform that encloses the top of the housing and is structurally attached to the housing, the top platform comprising:
      i. a top layer comprising a deformable UVC transparent fluorinated film;
      ii. a bottom layer comprising a quartz sheet of a selected thickness and a support layer comprised of perforations which allow UVC light to pass through, wherein the bottom layer is capable of supporting at least 300 pounds;
      and wherein the top layer and the bottom layer are separated by a selected thickness;
      iii. sides that enclose the top platform; and
      iv. a UVC absorbent fluid having a viscosity range between about 1 and about 500 centipoises situated between the film and the sheet, the amount of the fluid chosen to provide a selected thickness;
   b. a UVC emitting device positioned between the bottom platform and the bottom layer of the top platform; and
   c. optionally a device adjacent to the housing for removing debris.

2. The device of claim 1, wherein the UVC transparent fluorinated film is a bag filled with the UVC absorbent fluid, wherein the bag is positioned inside the volume defined by the bottom layer and the sidewalls of the top platform and the bag is capable of being removably attached to the top platform.

3. A device for sanitizing objects, comprising:
   a. a housing comprising a bottom platform and sidewalls that enclose the sides of the housing and a top platform that is capable of enclosing the top of the housing and is structurally attached to one side of the housing by a means for hinging, the top platform comprising:
      i. a top layer comprising a deformable UVC transparent fluorinated film;
      ii. a bottom layer comprising a quartz sheet of a selected thickness and a support layer comprised of perforations which allow UVC light to pass through, wherein the bottom layer is capable of supporting at least 300 pounds; wherein the top layer and the bottom layer are separated by a selected thickness;
      iii. sides that enclose the top platform; and
      iv. a UVC absorbent fluid having a viscosity of between about 1 and about 500 centipoises situated between the film and the sheet, the amount of the fluid chosen to provide a selected thickness;
   b. a UVC emitting device positioned between the bottom platform and the bottom layer of the top platform; and
   c. optionally a device adjacent to the housing for removing debris;
   wherein the top platform is in a tilted, non-horizontal position when no pressure is applied and is capable of enclosing the housing when pressure is applied and further comprising a means for returning the top platform to the tilted, nonhorizontal position when the pressure is removed.

4. The device of claim 3, wherein the UVC transparent fluorinated film is a bag filled with the UVC absorbent fluid, wherein the bag is positioned inside the volume defined by the bottom layer and the sidewalls of the top platform and the bag is capable of being removably attached to the top platform.

* * * * *